United States Patent [19]
Radford

[11] Patent Number: 5,483,172
[45] Date of Patent: Jan. 9, 1996

[54] RADIO FREQUENCY MEASURING APPARATUS

[76] Inventor: David J. Radford, 6 Cobbleset Lane, Pinetown Natal, South Africa

[21] Appl. No.: 79,801

[22] Filed: Jun. 22, 1993

[30] Foreign Application Priority Data

Jun. 22, 1992 [ZA] South Africa ............... 92/4569A

[51] Int. Cl.$^6$ ................................. G01R 27/26
[52] U.S. Cl. ................ 324/693; 331/65; 324/685
[58] Field of Search ................. 324/652, 663, 324/682, 674, 675, 685; 73/61.43, 61.44; 331/65

[56] References Cited

U.S. PATENT DOCUMENTS

| | | | |
|---|---|---|---|
| 3,636,470 | 1/1972 | Oliver et al. ............... | 331/65 |
| 4,053,849 | 10/1977 | Bower et al. ............... | 331/65 |
| 4,426,616 | 1/1984 | Maier . | |
| 5,034,722 | 7/1991 | Premack ............... | 331/65 |
| 5,119,671 | 6/1992 | Kopera . | |
| 5,130,672 | 7/1992 | Watkiss et al. ............... | 331/65 |
| 5,198,777 | 3/1993 | Masuda et al. ............... | 324/675 |
| 5,261,270 | 11/1993 | Gonze et al. ............... | 324/685 |
| 5,291,534 | 3/1994 | Sakurai et al. ............... | 331/65 |

FOREIGN PATENT DOCUMENTS

| | | | |
|---|---|---|---|
| 0472767 | 3/1992 | European Pat. Off. . | |
| 0205757 | 1/1984 | Germany ............... | 324/652 |
| 61-233373 | 10/1986 | Japan . | |
| 6756316 | 8/1980 | U.S.S.R. ............... | 324/652 |
| 0938118 | 6/1982 | U.S.S.R. ............... | 324/675 |
| WO92/07251 | 4/1992 | WIPO ............... | 324/682 |

OTHER PUBLICATIONS

By P. Neelakantaswamy et al., "Miniature-electrode probe for conductivity measurements on electrolytic solutions or colloidal sols of small sample sizes", 1983, vol. 16, No. 12, pp. 1189–1193, Great Britain.

Primary Examiner—Maura K. Regan
Attorney, Agent, or Firm—Young & Thompson

[57] ABSTRACT

A device is provided for measuring dielectric constant and conductance of a material such as massecuite, the device including a pair of electrodes which are switchably connected to a tank circuit which includes a variable frequency oscillator operating at radio frequencies, and two reference frequencies are measured with the electrodes disconnected from the oscillator and two measurement frequencies with the electrodes coupled to the oscillator tank circuit, the differences between the reference and measurement frequencies being used to compute the inductance and dielectric constant or composition of the material. The frequency is modified by not more than about 10 MHz and may be achieved either by switchably introducing additional inductance or capacitance into the tank circuit to modify its frequency or by having the electrodes switchable between a pair or oscillators operating at known radio frequencies.

6 Claims, 1 Drawing Sheet

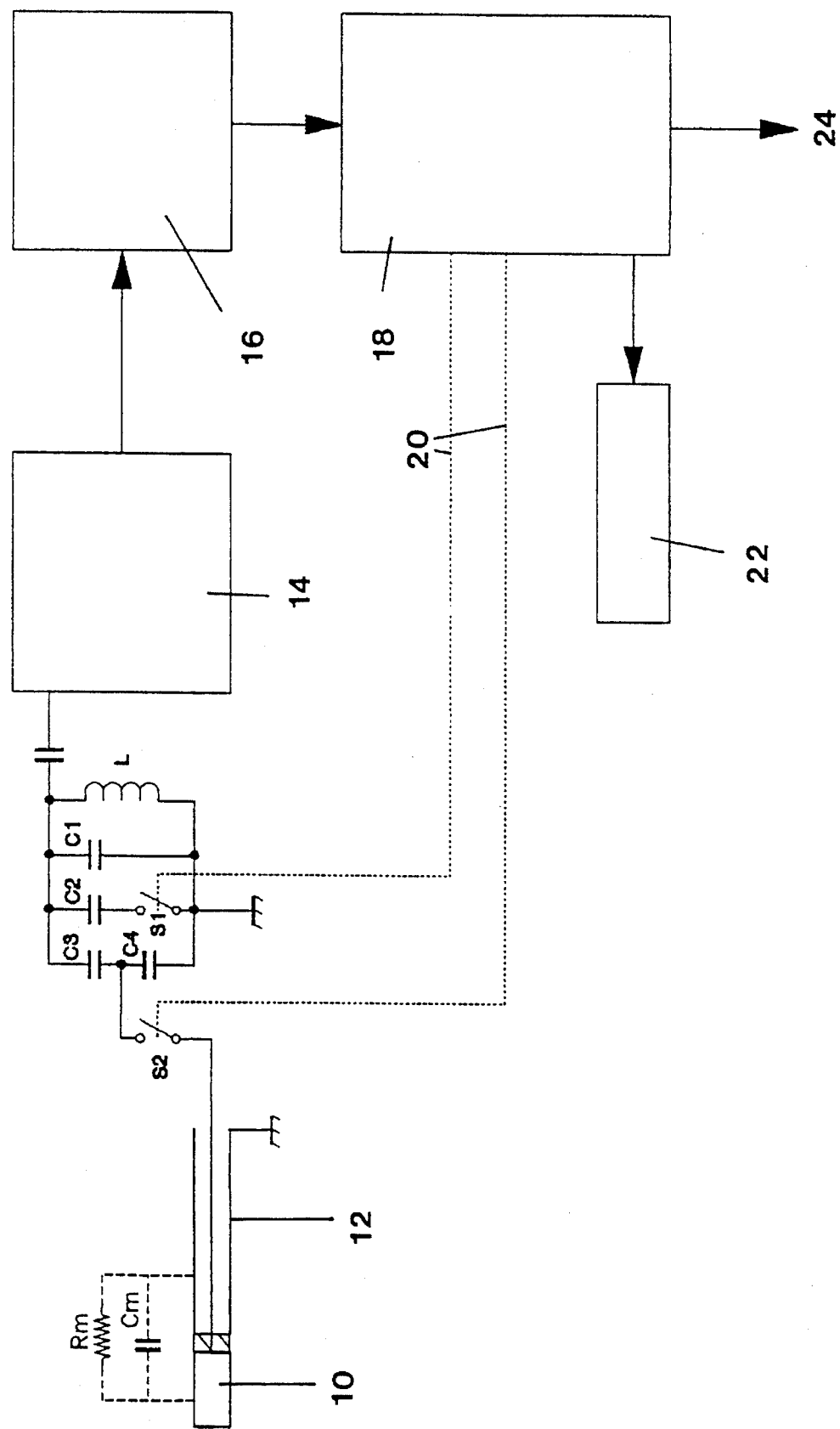

RADIO FREQUENCY MEASURING APPARATUS

BACKGROUND OF THE INVENTION

1. Field of the Invention

This invention relates to a device for measuring dielectric constant and conductance.

The composition of a material may often be characterised in terms of its dielectric constant or conductance. For example moisture content can often be correlated to the dielectric constant, while in solutions of ionic salts conductivity measurements are sometimes used to measure the concentration. Instruments which measure dielectric constant usually operate at radio frequencies where the capacitive reactance can more easily be measured.

It is an object of this invention to provide an instrument or device which is capable of providing direct measurements of both dielectric constant and conductance or alternatively may be calibrated to provide direct measurements of liquid composition where the relationship between liquid composition and dielectric constant and conductivity is unknown. A further object of the invention is to provide a device capable of a direct measurement of two components in solution; for example to provide direct measurements of both sucrose and ash and ionic salts in a solution containing both these substances.

The device of the invention has potential application in the sugar industry for the measurement or control of brix of liquors or massequites during pan boiling or measurement of ash in sugar refinery liquors.

2. Description of Related Art

The instrument also has general application in the chemical industry for measurement of moisture or solids on a variety of materials.

An EPO search revealed several patents as follows:

Dealing with these patents:

U.S. Pat. No. 5,199,671

This concerns a method for measuring the composition of a mixture of different fuels having different dielectric constants. The frequency of a variable frequency oscillator is determined when immersed but insulated from the fuel to be measured. The difference gives a measure of the dielectric constant of the fuels.

However, the difficulty of constructing an oscillator which is stable to temperature differences is well known so that if the temperature of either or any of the fuel changes, the measurements will be inaccurate. This inaccuracy is overcome in the present invention by using an electrode as the measuring element and having reference oscillator frequency measurements with the electrode in and out of circuit. In addition the present invention measures frequency shift at two oscillator frequencies allowing the composition to be related to complex impedances (dielectric constant and resistance).

U.S. Pat. No. 4,426,616

In this patent the capacitance of a probe is measured where there is parallel resistance across the capacitor. Fixed frequency generators are used as compared with the variable frequency oscillators of the present invention. The measurements are also of an analog nature as opposed to the present invention in which they are digital.

Publications

MINIATURE-ELECTRODE PROBE FOR CONDUCTIVITY MEASUREMENTS ON ELECTROLYTIC SOLUTIONS OR COLLOIDAL SOLS OF SMALL SAMPLE SIZES.

This instrument described is a miniature electrode for use where the quantity of sample is small (eg blood samples)

Measurement of conductivity is carried out at audio frequencies (10 kHz) using a system similar to that conventionally used for conductivity measurement.

MEASURING METHOD FOR ELECTROSTATIC CAPACITY

Appln. No. 60-75159

This invention involves a variable frequency oscillator for the measurement of capacitance where the unknown capacitor plus a known capacitor are alternatively switched into the oscillator circuit by a change over switch and the two frequencies measured.

From the two frequency measurements the value of the unknown capacitor can be calculated using a prescribed formula.

This apparatus is only useful for measuring capacitance provided there is no resistance in the measuring element.

PCTAU91/00467

This invention measures moisture and salinity.

Two electrodes are connected across an inductance to form a tank circuit of a variable frequency oscillator where the oscillator frequency varies according to the physical properties of the material between and surrounding the electrodes.

There are two modes of operation, one where a certain value of inductor is switched into circuit which results in the oscillator operating at a frequency of around 150 MHz. At this frequency, the shift in oscillator frequency due to varying soil conductivity is small in comparison with that caused by changing soil moisture (resulting in changing dielectric constant). This measurement is therefore representative of soil moisture.

In the second mode of operation, the inductor is replaced by a larger value inductor such that the frequency of oscillation is reduced to about 10 MHz. At this frequency the oscillator frequency is affected by both soil conductivity and moisture content (dielectric constant). By measuring the oscillator frequencies at both modes and calculating a difference, it is claimed that a signal representative of conductivity can be derived.

The differences between this and the present invention are as follows:

i) In the above invention, the electrodes are connected directly across the inductor. This will result in a fairly large frequency shift due to changing soil conditions, but this method will not work if the measurement system is used in a medium of high conductivity (such as low purity massecuites in sugar pans) since the Q of the circuit will be reduced (excessive damping) to a stage where the oscillator will not oscillate). The system will, however, probably work for measurement of moisture in cotton, grain, coal dust and concrete a claimed since these materials are not very conductive. To prevent loss of oscillation with highly conductive media, it is necessary to use a capacitive divider or some other means, to reduce coupling of the measurement electrodes to the tuned circuit. This, however, reduces the frequency shift of the oscillator due to material surrounding the electrodes.

ii) It is difficult to construct a variable frequency oscillator that is stable over a wide temperature range as is experienced in an industrial measurement environment.

Temperatures of the measurement instrument electronics can typically vary from 10° C. to 70° C.

The above instrument relies on an oscillator which is stable and only two frequencies (corresponding to the two modes) is measured. Any shift in oscillator frequency due to temperature variations (of the oscillator) will result in inaccuracy. Because of the high degree of coupling, the frequency shifts in the designed application are high, and drift in oscillator frequency may not introduce too significant an error. The degree of accuracy required for agricultural purposes is also not as high as that required for an industrial measurement instruments to be used for control.

In the present invention, the effects of oscillator drift are compensated for by switching the probe in and out of circuit and taking two measurements; a reference frequency measurement with the probe out of circuit, and a second measurement with the probe in circuit. The difference between these frequencies is used as the measurement. Since these two measurements are taken in succession (within a 2 second interval) and both measurements are subject to a similar drift, the effect of this drift is greatly reduced thereby increasing instrument accuracy.

A second set of measurements (measurement plus reference) is taken at a frequency about 10 MHz different to the first.

EUROPEAN PATENT NO. 0 472 767 A1

Vorrichtung zum Feststellen des Alkoholhaltes oder des Heizwertes eines Gemichs.

This patent describes a device used for measuring the alcohol content of fuel mixtures by measuring the dielectric constant conductance, and temperature of the mixture and then using these results to compute the alcohol content or calorific value of the fuel.

The patent covers the measuring cell which is described in detail and basically consists of two electrodes and a temperature sensor mounted in a housing through which the fuel is passed.

The capacitance is measured between the first electrode and the housing, and the conductance measured by the second electrode. A temperature sensor is installed in the first electrode.

The method of measuring the capacitance and conductance is not described in detail except that measurements are carried out at 10 MHz and that measurement takes 100 m secs.

The electronics are mounted in the probe assembly.

There appears no similarity between this invention and the present invention in which measurement is between two electrodes in the medium to be measured. The measurement system in the prior invention apparently only measures at one frequency.

SUMMARY OF THE INVENTION

According to the invention a device for measuring dielectric constant and conductance includes a pair of electrodes adapted to be immersible in the material to be measured, the electrodes being switchably coupled to the tank circuit of a variable frequency oscillator operating at radio frequencies, additional inductance or capacitance being switchably introducable into the tank circuit to modify the frequency, or the electrodes being switchable between a pair of oscillators operating at different known radio frequencies, where two reference frequencies with the electrodes disconnected from the oscillator and two measurement frequencies with the electrodes coupled to the oscillator tank circuit, are measured and the differences between the reference and the measurement frequencies are used to compute the inductance and dielectric constant or composition of the material.

A microprocessor may be used to switch additional inductance or capacitance in and out of the oscillator tank circuit, and to switch the probe or electrodes in and out of circuit to provide the two measurement and two reference frequencies. The microprocessor is programmed to calculate differences between the two measurement and reference frequencies and use these to compute one or more measurement signals representative of dielectric constant, electrical resistance, or composition of material surrounding the probe or between the electrodes.

The instrument may be calibrated in terms of known values of resistance and capacitance or material composition where the relationship between the two frequency differences, and the capacitance, resistance, or composition is determined by performing multi linear regression calculations and where this regression formula is programmed into the microprocessor to provide a measurement signal.

The frequencies may be measured by a digital frequency counter the output of which is fed into the microprocessor.

The microprocessor may be used to control the frequency counter.

The device of the invention may provide simultaneous measurements of two components in a multi component mixture.

Compensation of the measurement signal may be achieved by using the temperature measurement of the material being measured.

It will be appreciated that separate oscillators operating at different frequencies may be used as an alternative to switching additional inductance of capacitance to modify the frequency of a single oscillator where the electrodes are switched between the two oscillators.

Measurements may be carried out at two frequencies separated by about 10 mHz and by pre calibration and mathematical manipulation, a measure of an equivalent capacitance or resistance across the electrodes due to the material to be measured, or concentrator of one or two components in the material may be derived.

DETAILED DESCRIPTION OF THE INVENTION

The invention in it's preferred form is described below with reference to FIG. 1.

The electrodes are in the form of a probe consisting of two parts, a probe tip 10 and a probe body 12 separated by an insulating material. This is inserted into the side or bottom of a vessel or into a pipeline containing the material to be measured. The probe body is usually electrically connected to the vessel or pipeline through a fitting whereby the probe is inserted into the vessel or pipeline.

The probe tip and probe body including the walls of the vessel constitute two electrodes between which measurement takes place.

The effect of electrical conductance and dielectric constant of the material surrounding the probe may be considered equivalent to a resistance Rm and capacitance Cm connected across the probe.

The probe tip is connected through a switch S2 to a capacitive divider consisting of capacitors C3 and C4 which couple the probe to an inductor L which forms part of the resonant circuit of a variable frequency oscillator 14. The inductor L has a capacitor C1 connected across it and a second capacitor C2 in series with switch S1.

The variable frequency oscillator 14 provides an output signal which is fed to a digital frequency counter 16 where the frequency of oscillation is measured. The frequency of the oscillator determined by the inductance L and the following combinations:

1. When S1 and S2 are open the frequency is determined by the values of L, C1, and C3 and C4. This frequency is designed F1 which typically may be about 30 mHz.

2. When S1 is open and S2 is closed the frequency is determined by L, C1, C3, C4, and the probe including the resistance and capacitance Rm and Cm across the electrodes due to the material to be measured. This frequency is designated F2 which is slightly different to F1.

3. When S1 is closed and S2 open the frequency is determined by L, C1, C2, and C3 and C4. This frequency is designated F3 which typically may be about 20 mHz.

4. When S1 and S2 are closed, the frequency is determined by L, C1, C2, C3, C4 and the probe including the resistance and capacitance Rm and Cm across the electrodes due to the material to be measured. This frequency is designated F4 which is slightly different to F3.

Frequencies F1 and F3 are used as references since they are not affected by the probe.

When the probe is switched into circuit by closing switch S2, the frequency of oscillation is slightly changed due to influence of capacitance and resistance of the material across the probe combined with the impedance of the probe itself. Frequencies F2 and F4, where the probe is connected into the circuit, constitute two measurement frequencies.

While in theory the two measurement frequencies may be used to derive the values for the resistance and capacitance across the probe, in practice the variable frequency oscillator is prone to drift due mainly to the influence of temperature on the various components of the circuit. If this drift is significant in comparison to the changes in frequency due to changes in composition of material across the probe, then large errors in measurement will be introduced.

By introducing the reference frequencies F1 and F3 and considering differences F1–F2 and F3–F4 as the measurement signals the effects of this drift in the variable frequency oscillator can to a large extent to be eliminated since drift affects F1 and F2, and F3 and F4 similarly. The output of the variable frequency oscillator as measured by a digital frequency counter is fed into a microprocessor control unit 18 which has digital outputs 20 that are used to operate switches S1 and S2. The microprocessor is programmed to operate switches S1 and S2 in combination and sequence, take readings of F1 F2, F3 and F4 at the appropriate time, and calculate differences F1–F2 and F2–F3.

The probe may be calibrated in terms of resistance and capacitance by connecting combinations of standard resistors and capacitors in parallel across the probe and taking a series of measurements of F1–F2, and F2–F3.

By performing a multi linear regression a relationship between capacitance or resistance and F1–F2 and F2–F3 is established. Typically this relationship may be as shown below:

$$Z=A+B.(F1-F2)+C.(F1-F2)^2+D.(F1-F2)^3+E.(F3-F4)$$
$$+F.(F3-F4)^2+G.(F3-F4)^3.$$

Where Z=property to be measured (resistance or capacitance) A,B,C,D,E,F,G are constants determined by the multi linear regression.

Alternatively and preferably, the probe may be calibrated directly against known compositions of material to be measured and a relationship between the component to be measured and the two frequency differences established as above.

The microprocessor is programmed with this relationship and the value Z used as the required measurement signal which may be displayed on a digital display readout 22 and outputted 24 for use in a control system.

The microprocessor may be programmed to carry out two separate calculations to provide two separate measurements of different components which may be outputted separately.

Where the product to be measured is subject to temperature changes which affect measurements, a temperature signal may be inputted to the microprocessor and the necessary compensations introduced.

I claim:

1. A device for measuring a composition of a material comprising:

a pair of electrodes immersed in the material to be measured which are switchably coupled to the tank circuit of a variable frequency oscillator operating at radio frequencies through means for reducing damping of the tank circuit;

additional capacitance or inductance switchably introduced to modify the frequency of the tank circuit to thereby form two frequencies which are measured with the electrodes connected to the oscillator, whereby errors due to oscillator drift are minimized by intermittently taking a succession of frequency measurements followed by reference frequencies with the electrodes disconnected from the oscillator, a time difference between frequency measurements being of the order of seconds; and means for computing the differences between the measured and reference frequencies and using these differences to derive at least one signal representative of the composition of the material being measured.

2. Device according to claim 1, wherein a microprocessor is used to switch the additional inductance or capacitance in and out of the oscillator tank circuit, and to switch the electrodes in and out of the tank circuit to produce the two measurement frequencies and the two reference frequencies.

3. Device according to claim 2, wherein the microprocessor is programmed to calculate differences between the measurement and reference frequencies and to compute at least one measurement signal representative of one of the group comprising dielectric constant, electrical resistance, and composition of the material between the electrodes.

4. Device according to claim 1, wherein separate oscillators operating at different frequencies are used as an alternative to switching additional inductance or capacitance into the tank circuit to modify the resonating frequency of the variable frequency oscillator.

5. A device for measuring a composition of a material comprising:

a pair of electrodes immersed in a material to be measured which are switchably coupled to tank circuits of two variable frequency oscillators;

means for reducing damping of the tank circuits;

means for measuring two frequencies with the electrodes connected to the oscillator, errors due to drift of the oscillators being minimized by intermittently taking a succession of frequency measurements followed by reference frequencies with the electrodes disconnected from the oscillator, the time differences between frequency measurements being of the order of seconds;

means for calibrating the device against materials of known compositions; and means for computing a difference between the measured and reference frequencies to produce at least one signal representative of the composition of the material being measured.

6. Device according to claim 5, further comprising a microprocessor used to switch additional inductance or capacitance in and out of the oscillator tank circuits, and to switch the electrodes in and out of the tank circuit to produce the two measurement and two reference frequencies.

* * * * *